(12) United States Patent
Hinchman

(10) Patent No.: US 12,038,448 B2
(45) Date of Patent: Jul. 16, 2024

(54) SYSTEMS AND METHODS FOR PROVIDING QUALITY ASSURANCE FOR VALIDATION OF CALIBRATION DATA

(71) Applicant: Walter LLC, Reno, NV (US)

(72) Inventor: Walter J. Hinchman, Farmington, NM (US)

(73) Assignee: Walter LLC, Reno, NV (US)

( * ) Notice: Subject to any disclaimer, the term of this patent is extended or adjusted under 35 U.S.C. 154(b) by 356 days.

(21) Appl. No.: 17/490,982

(22) Filed: Sep. 30, 2021

(65) Prior Publication Data

US 2023/0107733 A1    Apr. 6, 2023

(51) Int. Cl.
*G01N 35/00*    (2006.01)

(52) U.S. Cl.
CPC . *G01N 35/00693* (2013.01); *G01N 35/00613* (2013.01); *G01N 35/00732* (2013.01); *G01N 2035/00702* (2013.01); *G01N 2035/00841* (2013.01); *G01N 2035/00851* (2013.01); *G01N 2035/0091* (2013.01)

(58) Field of Classification Search
None
See application file for complete search history.

(56) References Cited

U.S. PATENT DOCUMENTS

| | | | | |
|---|---|---|---|---|
| 2003/0033092 A1* | 2/2003 | Bush | ...................... | G16H 50/50 |
| | | | | 702/25 |
| 2006/0255257 A1* | 11/2006 | Belgovskiy | ............ | G01N 30/86 |
| | | | | 250/282 |
| 2010/0082279 A1* | 4/2010 | DeSimas | ................ | G01N 33/00 |
| | | | | 702/182 |
| 2012/0197571 A1* | 8/2012 | DeSimas | ................ | G01N 31/00 |
| | | | | 702/85 |
| 2012/0295361 A1* | 11/2012 | Cerda | .................. | G01N 33/743 |
| | | | | 436/131 |
| 2023/0204544 A1* | 6/2023 | Grebe | ................. | H01J 49/0009 |
| | | | | 250/282 |

OTHER PUBLICATIONS

CH. Aparna and D. Gowrisankar, A Review on Calibration of Analytical Instruments, IJPCBS 2015, 5(3), 572-582 (Year: 2015).*

* cited by examiner

*Primary Examiner* — Lina Cordero
(74) *Attorney, Agent, or Firm* — Mark A. Goodman; Goodman Law Center (57) ABSTRACT

A system and method for calibration of analytical instruments includes a software application allowing users to compute, construct, display, review, select and evaluate initial calibration models. The software application summarizes the initial calibration using the method evaluation parameters and the user selected evaluation criteria in the initial calibration evaluation table. The software application is a mathematically based program that will independently compute, construct, and display the initial calibration for each target analyte. This program then uses logic functions to review and select calibration variables against evaluation parameters. The software application is a user friendly tool performing all of the calculations independent of the on-boarded software and displays that information on a novel data visualization platform. The software application is the answer to questions centering around software limitations users encounter with on-board instrument software.

14 Claims, 3 Drawing Sheets

SYSTEMS AND METHODS FOR PROVIDING QUALITY ASSURANCE FOR VALIDATION OF CALIBRATION DATA

CROSS-REFERENCE TO RELATED APPLICATION

This is a Nonprovisional Utility U.S. Patent Application 10 under 37 CFR 1.53(b).

BACKGROUND OF THE INVENTION

1. Field of the Invention

The present invention relates generally to calibration of analytical instruments. More particularly, the present invention relates to software systems which enable users to quickly compute, construct, display, review, select and evaluate initial calibration models.

2. Description of Related Art

A laboratory relies heavily on analytical test equipment as a key component to help ensure the quality of reported data. The problem is human error. If your analytical bench chemists fail to make the proper initial calibration decisions your data quality suffers. The production of high-end quality data is a common goal shared by all analytical laboratories. However, one of the greatest short comings of analytical laboratories is the consistent production of high-end quality analytical data.

In principle, laboratories seek to build quality systems to produce high-end quality analytical data by minimizing random and systematic errors. Most established initial calibration acceptance criteria are established as a minimum pass/fail criteria: therefore, not all calibrations are created equal! Therefore, if a laboratory could consistently achieve higher quality calibrations, the quality of the reported data is equally improved upon. Higher quality data then drives data confidence while improving the laboratory-client relationships resulting in higher corporate profits while minimizing liability exposure! Better data leads to better decisions.

The source of that confidence is the specified accuracy of each instrument and the foundation of that accuracy is the initial calibration. Ultimately, the bedrock beneath that foundation of all analytical laboratories is the decisions made during the calibration of laboratory instruments. The evolution of analytical instruments and their associated data software program designs are in-large-part being driven by regulatory agencies requiring lower reporting limits while also achieving better accuracy and precision. Instrument manufacturers are responding with advances in instrument technology that can produce those data quality requirements which drives laboratories to purchase and/or replace aging instruments.

Instrument manufacturers are focusing their engineering efforts in the areas of producing user-friendly data handling solutions that are combined with smart instruments while miniaturizing the bench footprint. This approach, incorporating artificial intelligence, is designed to help improve preventive maintenance, lower the cost of ownership, and simplifying the workflow, i.e, designing a turnkey solution for analytical laboratories.

Analytical instrument design engineers are focusing their efforts on functions such as automatic leak checks and troubleshooting diagnostics, which allow operators to achieve better and faster results with fewer mistakes. These innovative software and hardware instrument improvements are specifically designed to pro-actively guide users through preventative maintenance steps to help reduce unplanned downtime and sample reruns, greatly improving productivity.

Yet, as the manufacturing industry has evolved with changing technology, an added burden has also been placed on the analytical chemist and laboratory management to ensure they can meet these more stringent method and regulatory requirements. Instrument data acquisition and quantitation software purchased with these instruments has taken a back seat to the primary instrument technology and has not kept pace with the changing market demands. While instrument software has advanced to handle hardware design changes, it has not kept pace with an innovative software upgrade to validate the data.

Historically, calibration models were typically selected using either an average response factor or a liner calibration model when building an initial calibration, where the instrument response is directly proportional to the concentration of the target analyte. These types of calibration models have some advantages, among them, simplicity and ease of use. However, as regulatory requirements have become more stringent, instrument technology has also had to evolve to keep pace with those requirements, (i.e., increase sensitivity and selectivity, linear dynamic range, etc.) With the evolving regulations and technology, analysts are increasingly likely to encounter situations where a linear model neither applies nor is appropriate; making calibration decision much more difficult for the bench analyst.

Most major manufacturers of gas chromatography (GC), liquid chromatography (LC) or ion chromatography (IC) instruments which produce chromatographic data have designed their software to use up to nine (9) distinct calibration models for data quantitation. These calibration models are as follows: Average Response Factor (A), Least Squared Equal Weighting (LS), Least Squared Inverse Concentration Weighting (LSIC), Least Squared Inverse Squared Concentration Weighting (LSISC), Least Squared Forced Zero (LSF0), Quadratic Equal Weighting (Q), Quadratic Inverse Concentration Weighting (QIC), Quadratic Inverse Square Concentration Weighting (QISC), and Quadratic Forced Zero (QF0).

Secondly, with a plethora of instrument manufactures they also produce final data in various digital formats such as: text files; excel files; CSV files; or other comma delineated files etc. Question (1): With a large variety of instrument manufacturers and final data formats, is it possible to find a program that could capture this variety of calibration data into a single software program to check mathematical calibration models? Model considerations: It is important to note that not all mathematical models are allowed by regulatory bodies and/or auditing agencies; some instrument manufacturers have designed their software to allow only certain calibration models, thus limiting the initial calibration choices analyst have when quantitating sample data; and there is no common naming scheme between manufacturers, which can cause major consternation for data users.

In fact, without an industry wide naming scheme, there have been instrument software revisions that have completely misnamed the mathematical models, where an analyst may be thinking they have chosen one model and in truth it may have been a calibration model completely different. Question (2): How can the analyst verify the calibration model chosen from the selection of on-boarded calibration models is the actual named calibration model chosen? Question (3): How can the analyst verify and validate the mathematical calibration models chosen from the selection of on-boarded calibration models are mathematically correct?

The calibration of analytical instruments producing chromatographic, spectrophotometric or other similar types of data, generally requires delineating or modeling the relationship between the response of the instrument and the concentration or mass of an analyte introduced into the instrument. Most instrument software will produce a graphical depiction of this relationship and is often referred to as the calibration curve.

When building a new analytical method, the type of calibration must be considered, as it plays a critical role in data quantitation. There are two major types of instrument calibration, that are used in the quantitative analysis of chromatographic data: a) external standard calibration, and b) internal standard calibration. The analyst that constructs a curve must navigate a number of key decision points in the evaluation and final choice of the mathematical model chosen for calibration. Each mathematical model has evaluation parameters that need to be reviewed to assess precision and accuracy such as Relative Standard Deviation (RSD), Relative Standard Error (RSE), minimum Response Factor (RF), correlation coefficient (r) or coefficient of determination ($r^2$). These evaluation parameters or mathematical functions also have evaluation criteria specified for each evaluation parameter which establishes a minimum pass/fail threshold to use a particular calibration model.

Question (4): How can the analyst, construct, review, select and evaluate a calibration model when RSE, (PE %), minimum RF, etc. are not calculated by the on-boarded instrument software? Question (5): The analyst generally requantitates the initial calibration standards against itself as a means to guesstimate the calibration metrics for the purpose of making final model decisions. This process is riddled with potential mistakes and is extraordinarily inefficient. How can the analyst ensure calibration models evaluations can be evaluated, verified, and validated?

Initial calibration for chromatographic methods involves the analysis of standards containing target analytes at varying concentrations defining the working or calibration range of the instrument. Samples are then analyzed on the instrument that has been configured to identify these target analytes and calibration models developed to produce concentration values based on the chosen mathematical calibration model. Question (6): How can the analyst verify initial calibration standards have been correctly prepared and ensure the construction of the calibration does not contain a rogue standard(s)?

Standards are generally prepared by serial dilution of a stock standard and will form a geometric series of concentration points where each standard will vary from adjacent standards by a constant factor. However, this may produce relatively wide spacing of the higher concentration standards in the geometric series masking the situation where the detector is reaching saturation. Analytical procedures which contain a large analyte list may have target analytes that are at saturation and need to be dropped from the initial calibration while retaining those same concentration points for other target analytes. Question (7): How can the analyst understand analyte saturation as well as calibration concentration spacing? Most regulatory agencies specify the minimum number of calibration standards for average response factor or linear (first order) calibration models and for quadratic (second order calibration models). Question (8): How can the analyst ensure the minimum number of calibration standards have meet the method criteria for each target analyte?

Once the calibration points have been chosen, the concentration points within the initial calibration define the working range of the instrument where the highest level calibration standard establishes the upper level of quantitation. The lowest calibration standard that is analyzed during the initial calibration generally must be at or below the established reporting limit and is considered the Lowest Level of Quantitation (LLOQ) or Reporting Limit (RL). The concentration of this standard is related back to sample concentration using sample size, dilution, and final volume. Therefore, the initial calibration must contain at least one standard at or below the calculated reporting limit. Currently, using on-boarded instrument software, this is a manual evaluation and most likely is not being evaluated at all. Question (9): Most calibrations are constructed using concentration units such as ug/L (PPB) or ug/ml (PPM). Samples typically undergo some type of extraction or preparation prior to sample analysis where a multiplier is applied to the concentration units generated during the final report generation. Since there is typically a sample multiplier, how can the analyst ensure the lowest calibration standard included in the construction of the initial calibration is at or below the required reporting limit?

Analysts generally prepare calibration standards that cover the concentration ranges appropriate for programs, projects, or particular types of analyses. Extrapolation of the calibration to concentrations either above or below those of the actual calibration standards are generally not appropriate as they may lead to significant quantitative errors regardless of the calibration model chosen. When calibration models are evaluated with current instrument software, users don't know if the LLOQ/RL will generate a positive concentration value, (i.e., a positive y-intercept.) The only option open to users is to requantitate the initial calibration against itself. In addition, many laboratories are required to report data below their actual reporting limit and/or report down to their statistically derived method detection limit as an estimated value. Question (10): How is an analyst able to prove data reported below their lowest calibration point is: a) at a concentration value that is above the y-intercept and will produce a positive value, b) the calculated concentration follows the predicable monotonic mathematical model, and c) a zero (0) response does not produce a calculated concentration that is above the LLOQ/RL?

Many regulatory programs are requiring laboratories to review their initial calibration curve for bias by performing a curve refitting inspection. This is generally not an alternative to evaluating the initial calibration mathematical model selection, using the historically accepted practice, i.e., RSD, correlation coefficient (r) or coefficient of determination ($r^2$), but is used only to help inspect and evaluate the calibration curve. There are two general approaches to inspect the calibration curve, and both curve refitting procedures evaluate the difference between the measured amount and the true amounts used to create that model. These two procedures are the calculation of Percent Error (PE %) or bias and Relative Standard Error (RSE %). Question (11): How can the analyst ensure the initial calibration has been reviewed and verified for curve refitting criteria?

Current laboratory instrument software serves a very utilitarian purpose and is generally grounded in good software engineering and proven calibration mathematics. However, most chromatography software employs a myopic data visualization approach and software engineers have failed to update the architectural design structure of this software in keeping pace with advancing and changing technology. The data is presented in a format that is clumsy, inefficient, is not well organized, it does not include all of the calibration metrics most laboratories are seeking and needs a visionary new look. In general, there are few arguments regarding calibration model mathematics; however, there are issues that should be addressed regarding three key functional areas: 1) better data visualization, 2) understanding how to take current software acquired initial calibration data, i.e., "raw" data and evaluate it in a manner allowing analyst to make better calibration decisions, 3) increasing data quality through better calibration decisions.

Consumers of Analytical Data. A sampling of some of the industries and agencies involved in the consumption of this type of analytical data are as follows: Environmental Chemistry (EPA), Safe Drinking Water Act (SDWA), Clean Water Act (CWA), Resource Conservation and Recovery Act (RCRA), Clean Air Act (CAA), Food and Drug Administration (FDA), Pharmaceutical drug production and oversight, Veterinarian drug production and oversight, Cosmetic industry, Food industry, Medical clinical laboratories, Nutraceutical laboratories, Center of Disease Control and Prevention (CDC), Governmental research laboratories, Infections and emerging disease laboratories, Federal Trade Commission (FTC), Dietary supplements, Bureau of Consumer Protection, Import/export chemical oversight, Department of Energy (DOE), Clean Renewable Energy Research Laboratories from solar, wind, water, geothermal, biomass and nuclear, Fuel and hydrogen cell laboratories, Department of Defense (DoD), New and emerging technical research laboratories, Materials Science laboratories, Explosive and high energy laboratories, Fuel laboratories, Weapons research laboratories, Additional National Security Agencies with Laboratory facilities, National Security Agency (NSA), Central Intelligence Agency (CIA), US Department of Homeland Security (DHS), National Drug Enforcement Administration (DEA), Federal Bureau of Investigation (FBI), National Oceanic and Atmospheric Administration (NOAA), Research laboratories, investigating airborne environmental issues, Research laboratories investigating long term analyte monitoring, Department of Interior, U.S. Geological Survey (USGS), Economic ore deposit research laboratories, Environmental research laboratories, United States Department of Agriculture (USDA), Pesticide and herbicide residue and research laboratories, Agriculture Marketing Services (AMS) laboratory testing to facilitate domestic and international marketing of food and agricultural commodities, Hemp licensed laboratory testing, State regulated Industries, Marijuana testing facilities, State toxicology laboratories, Private Industry, such as manufacturers etc., University laboratories and associated government funded joint projects, globally to all countries and industries. It should become apparent the significance surrounding the quantification of analytical data produced from these types of industries and agencies. The production of both accurate and precise data could not be more important when we consider the profound implications of how this data is being produced, reviewed, audited, regulated, reported, and consumed.

There is a demonstrated need in the field for a system and method for solving the aforementioned problems and for providing quality assurance for validation of calibration data.

SUMMARY OF THE INVENTION

The disclosed system and method implements a software application that incorporates these novel architectural software design features which allow the user to quickly compute, construct, display, review, select and evaluate initial calibration models. The software application independently calculates the initial calibration mathematical models for each target analyte using the "raw" data uploaded into the software as a solution (SAAS) application. This software produces true independent validation of the initial calibration. The software application summarizes the initial calibration using the method evaluation parameters and the user selected evaluation criteria in the initial calibration evaluation table. This allows the user to identify initial calibration data issues as well as final documentation of the initial calibration.

The software application as a mathematically based SAAS program will independently compute, construct, and display the initial calibration for each target analyte. This program then uses logic functions to review and select calibration variables against evaluation parameters. The software application then takes a metadata approach using logic functions to evaluate, validate and document all major and minor construction variables chosen by the user for each target analyte. The software application is a user friendly tool performing all of the calculations independent of the on-boarded software and displays that information on a data visualization deck (DVD), i.e. platform, that is truly unique. The software application is the answer to questions centering around software limitations users encounter with on-boarded instrument software.

These and other features and advantages will be apparent from reading of the following detailed description and review of the associated drawings. It is to be understood that both the forgoing general description and the following detailed description are explanatory and do not restrict aspects as claimed.

DETAILED DESCRIPTION OF EMBODIMENTS

The following descriptions relate principally to preferred embodiments while a few alternative embodiments may also be referenced on occasion, although it should be understood that many other alternative embodiments would also fall within the scope of the invention. The embodiments disclosed are not to be construed as describing limits to the invention, whereas the broader scope of the invention should instead be considered with reference to the claims, which may be now appended or may later be added or amended in this or related application. Unless indicated otherwise, it is to be understood that terms used in these descriptions generally have the same meanings as those that would be understood by persons of ordinary skill in the art. It should also be understood that terms used are generally intended to have the ordinary meanings that would be understood within the context of the related art, and they generally should not be restricted to formal or ideal definitions, conceptually encompassing equivalents, unless and only to the extent that a particular context clearly requires otherwise.

For purposes of these descriptions, a few wording simplifications should also be understood as universal, except to the extent otherwise clarified in a particular context either in the specification or in particular claims. The use of the term "or" should be understood as referring to alternatives, although it is generally used to mean "and/or" unless explicitly indicated to refer to alternatives only, or unless the alternatives are inherently mutually exclusive. Furthermore, unless explicitly dictated by the language, the term "and" may be interpreted as "or" in some instances. When referencing values, the term "about" may be used to indicate an approximate value, generally one that could be read as being that value plus or minus half of the value. "A" or "an" and the like may mean one or more, unless clearly indicated otherwise. Such "one or more" meanings are most especially intended when references are made in conjunction with open-ended words such as "having," "comprising" or "including." Likewise, "another" object may mean at least a second object or more. Thus, in the context of this specification, the term "comprising" is used in an inclusive sense and thus should be understood as meaning "including, but not limited to." As used herein, the use of "may" or "may be" indicates that a modified term is appropriate, capable, or suitable for an indicated capacity, function, or usage, while considering that in some circumstances the modified term may sometimes not be appropriate, capable, or suitable. A "computing device" can be a desktop, laptop, tablet, cell phone, and the like. "Plurality" is defined as more than one when used to describe a quantity in the description and claims.

Figure 1:
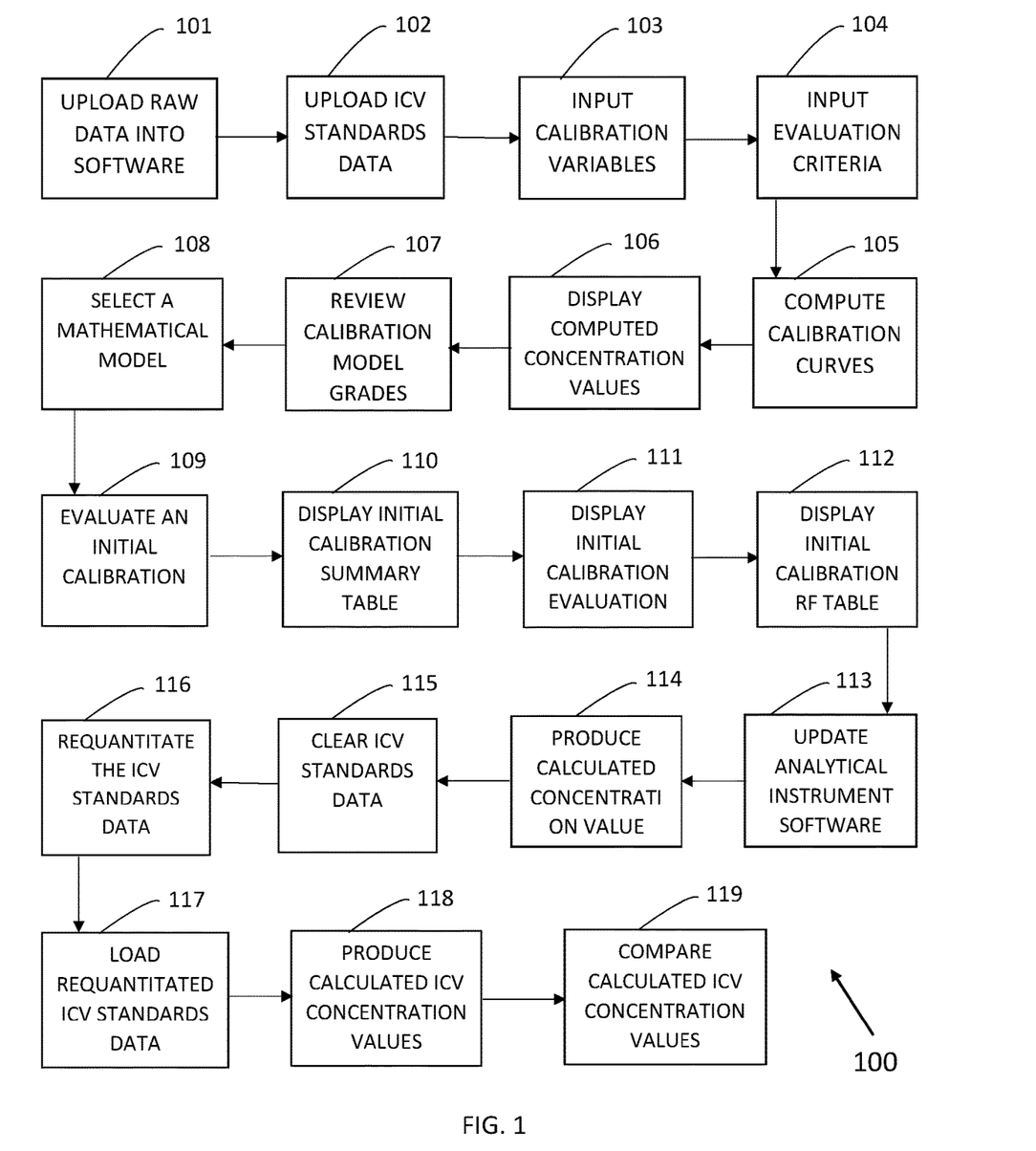
FIG. 1 illustrates a flow diagram of a system and method for providing quality assurance for validation of calibration data.
Figure 3:
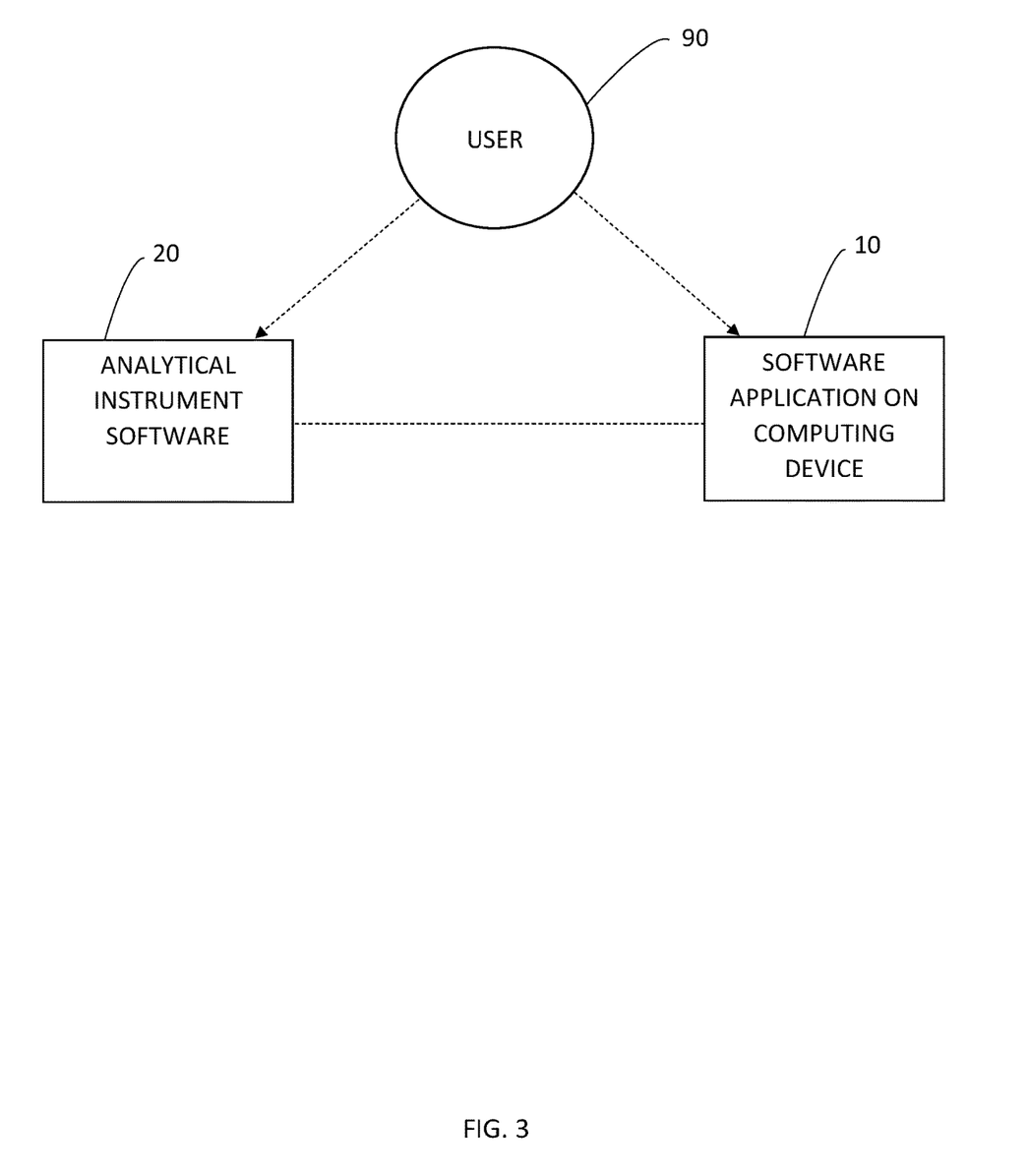
FIG. 3 is a diagram illustrating the relationship between a user, the software application, and the analytical instrument software

FIG. 1 illustrates a flow diagram of a system and method 100 for providing quality assurance for validation of calibration data. Referring to FIG. 3, a simple diagram illustrates the relationship between a user 90, the software application 10, and the analytical instrument software 20. The analytical instrument software 20 is installed on an analytical instrument while the software application 10 can be installed on a computing device (e.g. desktop or laptop computer).

With reference to FIG. 1, an analytical calibration instrument can include analytical instrument software 20 such as data acquisition software (e.g. on-board chromatography data system (CDS) software) designed to establish analytical calibration instrument parameters that will initially capture or acquire data. A first data set comprises raw data and includes a plurality of target analytes. Once a first data set is acquired by the analytical calibration instrument, a user 90 (e.g. chemist) can upload 101 this data into a method file in a software application 10 installed on a computing device. In this example, a first data set produced by the analytical calibration instrument is uploaded by the user 90 into a software application 10 (e.g. "Walter") in a calibration data worksheet. Each individual data point in the data set is opened, copied, and pasted into the appropriate calibration data point field. Each individual data point takes 20 seconds or less to upload. Depending on the total number of calibration data points in the data set, a typical calibration can be easily loaded into the software application 10 in less than five minutes. Example types of files that can be uploaded include: text files, CSV files, Excel files, comma delineated files, and the like.

The analytical calibration instrument can also acquire a second data set, wherein the second data set comprises initial calibration verification (ICV) standards and a plurality of target analytes. The second data set is a single data point, i.e. an independent standard prepared separately from the reference standards used to prepare the calibration. The second data set is a "sample" with known concentrations thereby independently verifying the efficacy of the calibration. When the second data set is acquired by the instrument, the user 90 can upload 102 this data into the software application 10.

After uploading the data sets, the user 90 can input 103 a plurality of calibration variables for constructing a calibration curve for each target analyte. The plurality of calibration variables can include: a) the user 90 can build an initial calibration (using up to twenty calibration points), b) each target analyte is mathematical modeled for nine separate mathematical calibration models using the selected calibration points, c) the software application 10 has the ability to eliminate or delete any combination of calibration points for each target analyte, d) the software application 10 allows the user 90 to input concentration values for each calibration point and for each target analyte.

The user 90 can input 104 evaluation criteria for evaluating the plurality of calibration variables against a plurality of evaluation parameters. The analytical instrument software 20 collects raw data and allows the user 90 to construct a calibration and to select a mathematical calibration model for each target analyte. CDS software 20 cannot evaluate an initial calibration but does produce some initial calibration parameters such as RSD, RF r and/or $r^2$. For example, the software application 10 can be configured to allow the user 90 to select fifteen individual calibration criteria for fifteen evaluation parameters. The construction parameters are evaluation criteria used for each target analyte. There can be more than fifteen types of evaluation criteria. For example, the evaluation criteria can include: 1) verifies initial calibration (ICAL) can meet aqueous matrix Reporting limit (RL) criteria, 2) verifies ICAL can meet soil RL criteria, 3) calculates RF for each individual concentration point as well as average RF of all ICAL points for each target analyte, 4) calculates the RSD, 5) verifies the RSD can meet criteria, 6) verifies if the selected mathematical calibration model can be used with the calculated RSD and meet criteria, 7) if minimum RSD fails, software checks to see if user 90 selected mathematical calibration model meets the minimum r or $r^2$ criteria, 8) verifies if the selected mathematical calibration model meets the minimum RF value criteria (SPCC compounds), 9) verifies if the selected mathematical calibration model meets the minimum RSD criteria for selected CCC compounds, 10) verifies if the ICAL meet the minimum number if ICAL points for an average RF model, 11) verifies if the ICAL meet the minimum number of ICAL points for a linear regression model, 13) verifies if the ICAL meets the minimum number of ICAL points for a quadratic regression model, 14) verifies if the minimum number of ICAL points passed the Bias or Percent Error (PE %) criteria, 15) verifies if the ICAL meet the minimum RSE % criteria, 16) Verifies if the second source ICV meet the minimum SPCC and CCC criteria, 17) verifies if the ICV calculated concentration from the on-boarded CDS software 20 matches the same concentration as the software application 10 using user 90 selected criteria. Aqueous and soil matrices are non-limiting examples of evaluation criteria. Other evaluation criteria and matrices can be included such as air, tissue samples, etc.

After inputting 104 evaluation criteria, the software application 10 can mathematically compute 105 the constructed calibration curves for each target analyte, using the plurality of calibration variables and a plurality of mathematical models. The software application 10 independently computes 105 the ICAL points using any combination of construction variables. The software application 10 requantitates each target analyte for every selected ICAL point in real time or on-the-fly. This is a substantial improvement over other CDS software which operates as follows: once the user 90 selects the ICAL construction parameters, each individual files must be re-quantitated against the new ICAL method file to view the calculated concentration for each ICAL point, one point at a time, and each target analyte.

The software application 10 includes a data visualization table (also called a data visualization deck). The data visualization deck (DVD) was developed so the user 90 could view the ICAL points for all mathematical models (e.g. nine models) for each target analyte and see how the calibration parameters change as the ICAL construction changes in real time or on-the-fly. Calculating all mathematical models for any combination of ICAL construction gives the user 90 unprecedented understanding of the mathematical modeling as well as decreasing the ICAL construction time, and enabling the user 90 to choose the best fit calibration model. The disclosed system and method is faster, more efficient, boosts the quality of reported data, and is independently validated by a mathematical based software as a solution (SaaS) program. After computing 105 the constructed calibration curves for each target analyte, the software application 10 displays 106 computed concentration values, using the raw data uploaded 101 by the user 90. The software application 10 displays 106 the computed concentration values for each target analyte, for a plurality of selected calibration points, and for a plurality of calibration models. The software application 10 can be modified to display different calibration information and is not limited to any particular architectural design.

A user 90 can review 107 the plurality of calibration model grades displayed in the data visualization table (DVD) and summarized in a report card for each target analyte. The DVD enables a user 90 to view all mathematical models (e.g. nine models) for all chosen calibration points and see the ICAL points requantitated in real time for each calibration construction variable change. The DVD also allows a user 90 to see the ICAL models and each calibration parameter re-calculated for each construction variable change, in real time or on-the-fly. The report card is placed on the DVD to rank and re-rank each calibration model as the user 90 changes the calibration construction variables. The software application 10 can be configured to only consider a few ICAL parameters for generating a report card, which enables a user 90 to make a quick decision. The report card can be changed or modified in numerous ways using different sets of calibration parameters. The calibration parameters can be ranked in various ways in the report card.

After reviewing 107 the plurality of calibration model grades, a user 90 can select 108 a mathematical model from the plurality of models for each target analyte. The software application 10 can be configured with a drop down menu allowing the user 90 to select one of the mathematical models. By using a drop down menu, the abbreviated name of the ICAL mathematical model can be used throughout the application 10. This allows the software application 10 to search for the parameters associated with the ICAL name. The ability of a user 90 to review and select from a drop down menu is an improvement in the field. For example, an instrument manufacturer could misname (mislabel) a calibration mathematical model. This mistake would go unnoticed, but the disclosed software is able to independently reconstruct the ICAL to verify and validate the mathematics. Also, some manufacturers use different terminology which is very confusing to the user 90 for selecting a mathematical model. If a user 90 is unable to understand the nomenclature, it is very difficult to know which mathematical model is represented by a particular nomenclature. The drop down menu of the disclosed software application 10 solves this problem.

After a user 90 selects 108 a mathematical model, the software application 10 can evaluate 109 an initial calibration (ICAL) using the selected model for each target analyte, and for the plurality of evaluation parameters using the previously inputted evaluation criteria. This evaluation 109 process is an improvement compared to other software in the field. Some calculators can process a non-weighted mathematical model for a few ICAL points, one at a time after being manually entered. However, there is no other software capable of evaluating weighted mathematical models other than the disclosed application 10.

The software application 10 can display 110 an initial calibration summary table. The ICAL summary table comprises evaluation metrics which include a plurality of evaluation parameters and the inputted evaluation criteria used during the initial calibration evaluation. For example, the first page of the summary table (report) documents the evaluation criteria chosen by the user 90 for each evaluation parameter that is used to conduct the ICAL evaluation. The software application 10 can also display 111 an initial calibration evaluation table, wherein the ICAL table comprises a list of: each target analyte and whether each target analyte passed (or failed) the plurality of evaluation parameters for the inputted evaluation criteria. For example, the ICAL table can list dozens of analytes (e.g. 72 compounds). The number of target analytes can vary without requiring any modifications to be made to the software application 10.

Additionally, the software application 10 can display 112 an initial calibration response factor (RF) summary table. The initial calibration RF summary table comprises a list of: each target analyte; the calculated RF for each target analyte; the plurality of evaluation parameters corresponding to each target analyte; and the user 90 selected ICAL mathematical model.

Further, the user 90 is able to update 113 the analytical instrument software 20. The updates can include: an analytical software method file; and the plurality of calibration variables identified by the software application as meeting the inputted evaluation criteria for the plurality of evaluation parameters for each target analyte. Updating the analytical instrument software enables a user 90 to make the most appropriate calibration construction decisions. This feature of the disclosed system 100 is in stark contrast to other CDS software that simply collects data and quantitates data after a user 90 has constructed a calibration curve. The problem with other CDS software is that the analyst constructs a calibration blindly without knowing the best fit calibration models to produce better quality data.

In the present system and method 100, once the on-board analytical instrument software 20 is updated 113 and configured with the calibration construction variables determined by the software application 10, the variables are used by the analytical instrument software 20 to quantitate the ICV. The analytical instrument software 20 produces 114 a calculated concentration value for each target analyte based on the plurality of evaluation variables corresponding to each target analyte. This is used to validate both the mathematics of the chosen calibration model and to ensure the analytical instrument software 20 calibration variables are correctly configured.

After the analytical instrument software 20 produces (requantitates) 114 calculated concentration values, the user 90 can clear 115 the second data set of ICV standards from the software application 10 that was previously uploaded 102. The analytical instrument software 20 can requantitate 116 the second data set of ICV standard data for each target analyte using: the updated analytical instrument software method file; and a calculated concentration value for each target analyte based on the plurality of calibration variables identified as meeting the inputted evaluation criteria of the plurality of evaluation parameters corresponding to each target analyte.

After the analytical instrument software 20 requantitates 116 the ICV standard data, a user 90 can load 117 the requantitated ICV standard data for each target analyte into the software application 10. Once the requantitated data is loaded 117, the software application 10 produces 118 a calculated ICV concentration value for each target analyte based on the plurality of calibration variables identified as meeting the inputted evaluation criteria for the plurality of evaluation parameters corresponding to each target analyte.

The software application 10 can compare 119 the calculated ICV concentration values produced by the analytical instrument software 20 and the calculated ICV concentration values produced by the software application 10. This comparison 119 serves several purposes: a) to help the analyst make the most appropriate calibration construction decisions, b) to make sure the analytical instrument (CDS) software 20 is correctly configured, and c) to mathematically validate the calibration models and configuration settings.

Figure 2:
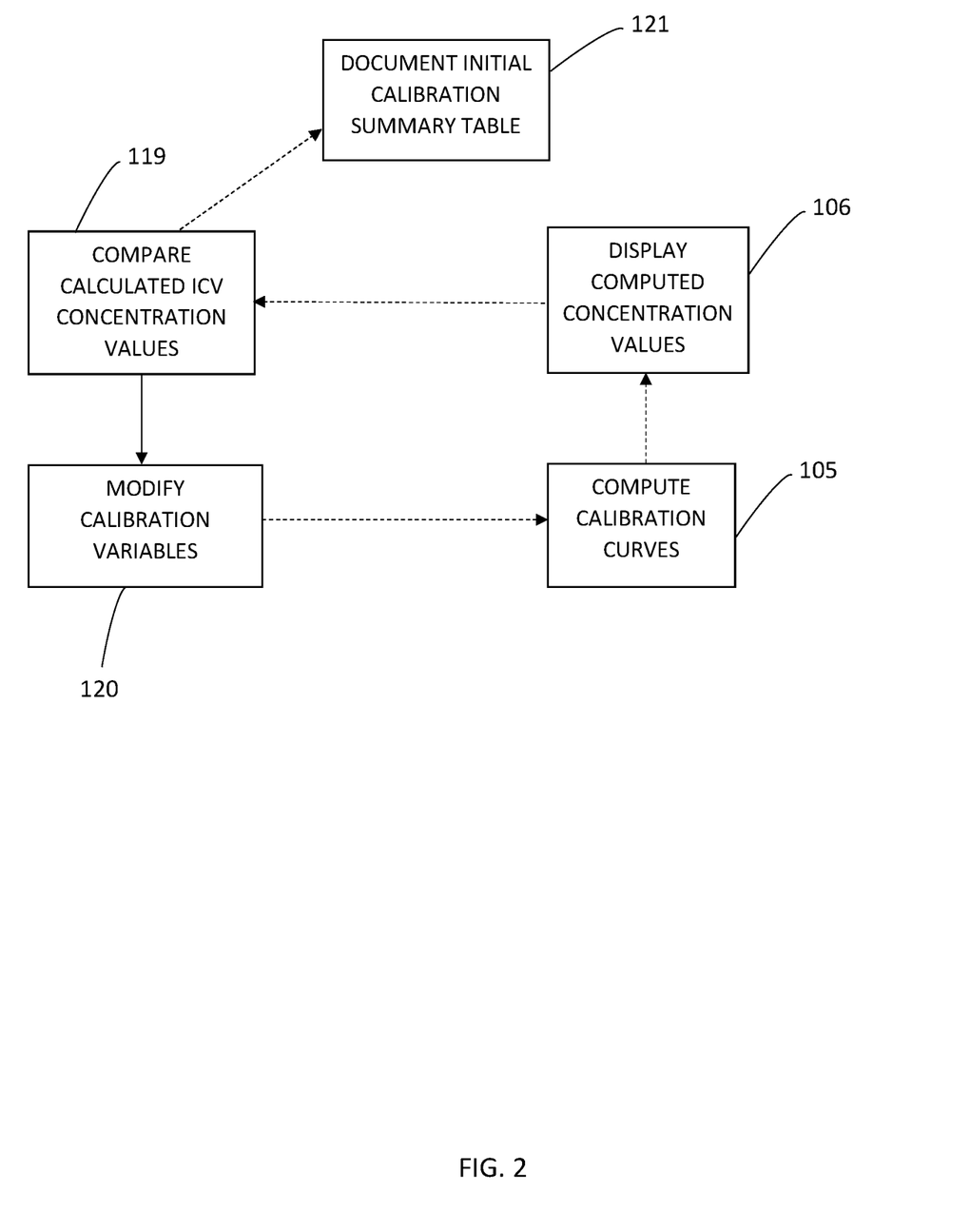
FIG. 2 illustrates an abbreviated flow diagram illustrating the steps of modification of calibration variables and documenting the initial calibration summary table.

Referring to FIG. 2, after comparing 119 the calculated ICV concentration values, the software application 10 can modify 120 one or more calibration variables, thereby improving initial calibration to ensure the evaluation parameters pass the inputted evaluation criteria. Once the calibration variables are modified 120, other steps of the system and method 100 are performed. For example, the software application 10 uses the modified calibration variables to mathematically compute 105 the constructed calibration curves for each target analyte. The software application 10 can also use the modified calibration variables to display 111 an initial calibration evaluation table, wherein the ICAL table comprises a list of: each target analyte and whether each target analyte passed (or failed) the plurality of evaluation parameters for the inputted evaluation criteria. Thus, the software application 10 substantially improves initial calibration.

Further, the software application 10 can document 121 the initial calibration summary table, wherein the initial calibration summary table displays final decisions detailing initial calibration. Documenting initial calibration is important for ensuring data integrity. Data integrity can only be claimed if one can reconstruct the historical records. Secondly, data integrity can only be claimed if those documents have a legally defined chain of custody (COC). The initial calibration summary table is a way of documenting the data files used in the initial calibration construction, as well as the chosen calibration construction variables and the chosen mathematical model. Thus, it is important to document 121 a summary table for tracing the original user 90 (analyst) and a data reviewer with their "wet" signature.

Typically, analytical instrument (CDS) software 20 can perform at least three types of calibrations including internal calibrations, external calibrations, and isotope dilution calibrations. The software application 10 can also be coded to perform internal, external, and isotope dilution calibrations. Further, the software application 10 can be configured (coded) to display 110 an initial calibration evaluation table comprising a list of: ranking the performance of the plurality of evaluation parameters for the inputted evaluation criteria.

The disclosed system and method 100 can further include an extrapolation calculator. For example, the software application 10 can take the lowest selected calibration point and uses the same modeling mathematics to extrapolate or predict the behavior of the curve as displayed in predicted concentration values of calibration points at 75%, 50%, 25%, 12.5% and zero area of the last real calibration point used in the construction of the calibration. The extrapolation calculator is a novel feature for providing mathematical driven, not statistical driven MDL, LOD, and sensitivity checks that are real numbers.

The software application 10 can be installed on a wide variety of computing devices and is not limited to any particular nomenclature. In one example, the software application 10 is named WLTR (or WALTER). WLTR is an example software application 10 that is designed and developed to provide instrument users a mathematically based platform to compute, construct, display, review, select and evaluate initial calibrations using a novel data visualization deck (DVD) summarized in an initial calibration summary table. This data-design structure is engineered to help aid the bench chemist, make better calibration decisions, produce better quality data and provide the analyst an evaluation tool or a Data Validation Assistant (DVA).

WLTR addresses the areas of weakness of prior systems in the field and the result is: a more efficient analyst, better calibration decisions producing higher quality data, a data quality mechanism and efficiency metrics to increase profitability, a fiduciary commitment to your owners, clients, and regulators by eliminating random and non-random errors; hence an insurance policy. WLTR incorporates numerous functions allowing the end user to manipulate the initial calibration construction. These calibration variables and evaluation parameters are encapsulated in the initial calibration summary table enabling the user to make mathematically based calibration decisions.

Software Uploads using Various Digital Formats. Question (1): With a large variety of instrument manufacturers and final data formats, is it possible to find a program that could capture this variety of calibration data into a single software program to check mathematical calibration models? WLTR is designed to electronically read and digitally incorporate a large variety of data formats into a single program; in the same manner as a Laboratory Information Management System (LIMS) is designed. WLTR can accommodate at least the following types of digital data formats: text files; excel files; CSV files; or other comma delineated files etc.

Calibration Model Nomenclature. Question (2): How can the analyst verify the calibration model chosen from the selection of on-boarded calibration models is the actual named calibration model chosen? First, WLTR can be written and coded to mathematically calculate the most common calibration models (e.g. nine models) used in chromatography software. Secondly, the acquired "raw" data used to construct or build an initial calibration is the same data uploaded into WLTR, so there is a direct digital data set used for both. Thirdly, WLTR can accommodate calibration points (e.g. twenty points), allowing data points to be deleted or manipulated in the same fashion as the on-boarded instrument software.

A key to verifying and identifying the named calibration model is quantitating an independent sample, (i.e., the initial calibration verification (ICV) standard against both calibrations.) The ICV is a standard typically purchased from a source of standards independent of the source used to prepare the initial calibration standards and its purpose is to verify the initial calibration standard was properly prepared. This standard has an added benefit when uploaded into WLTR; it is used to independently compare the computational mathematics produced by both software programs, (i.e., it independently validates the calibration mathematics.) Once digital data is uploaded, WLTR computes, constructs and displays all calibration points for the mathematical models. It can compute all initial calibration points quantitated against the constructed mathematical model and display the data for all the data points (e.g. twenty data points). On-boarded software (analytical instrument software) is not capable of these computations on-the-fly nor can they display all possible calibration models, or display all calibration points. Finally, WLTR also computes the ICV target analytes against the constructed initial calibration using the chosen calibration variables and displays the data quantitated against the mathematical models. The ICV target analyte value(s) of the on-boarded software is also displayed; therefore, the data set that has matching concentration values verifies the named mathematical model.

Calibration Mathematics Validation. Question (3): How can the analyst verify and validate the mathematical calibration models chosen from the selection of on-boarded calibration models are mathematically correct? WLTR independently computes all calibration models from the "raw" uploaded data. WLTR is used to evaluate all possible calibration variables that are then used by the analyst to modify the on-boarded instrument software to construct the instrument calibration. The analyst then requantitates the initial calibration verification (ICV) standard using the on-boarded revised method and uploads the newly requantitated ICV into WLTR. WLTR computes the concentration values for the ICV target analytes against all possible mathematical calibration models and displays the concentration determined by WLTR as well as the on-boarded instrument software. WLTR uses the Visual Data Deck (DVD) to display both sets of data and calculates the percent error (PE %) between these two values. The requantitated concentration values from the instrument on-boarded software will now produce the exact same calculated concentration values for each target analyte as calculated by WLTR for the selected calibration model. WLTR uses a specific proprietary process to validate the initial calibration by three metrics: 1) it verifies the initial calibration variables used in WLTR are also the same calibration variables selected for the on-boarded instrument software; 2) it verifies and validates the chosen mathematical model; and 3) it verifies and validates the mathematical functions and naming scheme.

Initial Calibration Construction Variables. Question (4): How can the analyst, construct, review, select and evaluate a calibration model when RSE, (PE %), minimum RF parameters are not calculated by the on-boarded instrument software? As discussed in section 2, Instrument Trends, the instrument manufacturing side has evolved significantly in the past several decades; incorporating artificial intelligence to help improve preventive maintenance, lower the cost of ownership, and simplifying the workflow, (i.e, designing a turnkey solution for analytical laboratories.) However, instrument software has not kept pace with the changing market demands, and manufacturers have not focused their software design efforts that would make a true QA/QC turnkey solution for analytical laboratories. WLTR was designed as a SAAS program that can evaluate both internal or external calibrations using uploaded "raw" data in a variety of digital or electronic formats.

WLTR was not designed as a concept or as a replacement to on-boarded instrument software, but was conceived and designed as a true working program. The need for such a software program to compute, construct, display, review, select and evaluate calibration data has never had a greater demand than for its use today. WLTR has incorporated five novel software design features that will empower the user to quickly assimilate data allowing unprecedented calibration decisions: a unique platform to review the initial calibration described as a Data Visualization Deck (DVD); The ability to change calibration variables, in real-time, and visualize how those changes affect the requantitation of each initial calibration point for all mathematical model options; A software feature that incorporates calibration evaluation parameters not currently programed into on-boarded instrument software, i.e., % RSD, PE %, SPCC, CCC etc.; A software feature that allows the user to input initial calibration criteria for each calibration evaluation parameter; and A software feature that performs an overall evaluation of the initial calibration for all evaluation parameter using the evaluation criteria input by the user. The result is a personal Data Validation Assistant (DVA), leading to better decision making and optimal data quality.

Initial Calibration—Requantitate Data In Real-Time without Manual Requantitation. Question (5): How can the analyst ensure calibration models are being properly reviewed, verified and validated before they are put into production? With on-boarded instrument software, the analyst must first collect the initial calibration data and start the process of calibration construction. This involves making construction decisions by viewing one analyte at a time, and scrolling through additional windows to see a calibration graph as well as RSD and correlation coefficient or r values. After the first rough calibration decisions are made, the analyst requantitates the standards against itself and gets a second look at the calibration. This is generally needed to help the analyst understand the calibration metrics in making final model decisions. This process is riddled with potential mistakes and is extraordinarily inefficient.

WLTR, with the five major software design features, allows the user to construct the initial calibration and/or modify the initial calibration and understand real-time how the calibration metrics change with each calibration decision point change. The RF, RSD and a host of many more calibration parameters are calculated and displayed in the data visualization deck (DVD) for each target analyte. As an example, if the RSD, for a target analyst is above an acceptance limit, the analyst may decide the RF value of one or more calibration points is producing the high RSD. WLTR will allow the analyst to easily eliminate any single calibration point or a combination of calibration points anywhere in the calibration. Each time a change is made the remaining calibration points are automatically requantitated on-the-fly for all the mathematical models as well as updating all of the calibration parameters. The analyst will know immediately, how these changes to the construction of the calibration affects the overall evaluation of the initial calibration. The process performed using the on-boarded instrument software is tedious, time consuming, riddled with possible mistakes, and is extraordinarily inefficient. WLTR is extraordinarily efficient, as it will evaluate, verify, and validate the initial calibration on-the-fly saving an enormous amount of time, and eliminating all possible evaluation mistakes while validating the calibration against the evaluation parameters.

Calibration Standards. Question (6): How can the analyst verify the initial calibration standards have been correctly prepared and ensure the construction of the calibration does not contain a rogue standard(s)? WLTR is designed with a multitude of unique software features allowing the user to efficiently conduct an initial calibration analyte response review, facilitating the search for suspected mis-made or rouge standards. There are two approaches the user could employ for this type of evaluation as follows: 1) WLTR has a built in data visualization deck (DVD) allowing, the user, unfettered viewing of the initial calibration construction. This includes the graphical depiction of five of the nine calibration curves for each target analyte. By scrolling through each target analyte and viewing these graphs, mismade, or rogue standards will be very apparent to the data viewer. 2) WLTR will display the calculated concentration values for each target analyte included in the initial calibration verification (ICV) standard loaded into the software. The end user selects the true concentration of this standard the same as for the true concentration of the initial calibration points. WLTR will evaluate the ICV against the criteria the user chooses, and a rogue standard could be found by reviewing the ICV for percent difference against the know true value, (i.e., a metrics evaluation.) WLTR will perform this evaluation instantaneously and will summarize and document the data in the initial calibration summary table.

Target Analyte Saturation and Initial Calibration Point Spacing. Question (7): How can the analyst understand analyte saturation as well as calibration concentration spacing? WLTR displays the calibration graphs along with the RF values allowing the analyst to see the direct correlation between these two items in the data visualization deck. The visualization of the calibration graphs directly associated with the RF values for each calibration point gives great data insight to both concentration spacing as well as analyte saturation.

Evaluating the minimum Number of Calibration Points. Question (8): How can the analyst ensure the minimum number of calibration standards have meet the method criteria for each target analyte? This is such an easy task one may wonder, why is this important? It becomes important when an analyst is calibrating a method with a large target analyte list where these minor calibration issues are easily overlooked. One of the five novel software design features incorporated into WLTR is a feature allowing the user to input, review, verify and validate calibration parameters not currently programed into on-boarded instrument software. The user can input the minimum number of calibration points needed to use for: an average RF calibration model, a linear regression calibration model, or a quadratic regression calibration model. WLTR will evaluate each target analyte, determine the mathematical model chosen, and count the number of calibration points the analyst chose for that calibration model. WLTR will then display its findings in the initial calibration evaluation table indicating if that set of calibration parameters met the criteria to allow its intended use.

Evaluating the Initial Calibration for Reporting Limit. Question (9): Most initial calibrations are constructed using concentration units such as ug/L (PPB) or ug/ml (PPM). Samples typically undergo some type of extraction or preparation prior to sample analysis where a multiplier is applied to the concentration units generated during the final report generation. Since there is typically a sample multiplier, how can the analyst ensure the lowest calibration standard included in the construction of the initial calibration is at or below the required reporting limit? WLTR allows the user to input, review, verify and validate calibration parameters not currently programed into on-boarded instrument software. The user can input the laboratory required reporting limit (LOQ/RL) for each target analyte for two separate matrices such as soil or water. The units used for the initial calibration are mathematically transformed into the reporting units established for the reporting limit using the multipliers for each matrix input by the user. WLTR will evaluate and display those findings in the initial calibration evaluation table indicating if the lowest calibration point chosen for a particular target analyte met the minimum reporting limit goal.

Extrapolation and Zero (0) Area. Question (10): How is the analyst able to prove data reported below their lowest calibration point is: a) at a concentration value that is above the y-intercept and will produce a positive value, b) the calculated concentration follows the predicable monotonic mathematical model, and c) a zero (0) response does not produce a calculated concentration that is above the LOQ/RL? WLTR, through the data visualization deck, allows the user to quickly assimilate data and review the requantitated or recalculated concentration value of each initial calibration point for all mathematical model options ensuring concentration values below the reporting limit will produce positive values. WLTR uses the lowest chosen calibration point and estimates concentration values below the lowest limit of quantitation standard at 0.75%, 0.50%, 0.25%, 0.125% and zero area for all calibration models by extrapolating the mathematical model residuals. Therefore, the estimated concentration values below the LOQ/RL can be proven to follow the monotonic mathematical model. WLTR estimates the zero (0) point concentration for each mathematical model and displays that information on the DVD. In addition, the chosen mathematical model linear dynamic range (LDR) study data for each analyte is summarized in the summary report to include the estimated concentration for the zero (0) area.

Curve Refitting. Question (11): I-low can the analyst ensure the initial calibration has been reviewed and verified for curve refitting criteria? WLTR calculates both RSE and PE % evaluation parameters which are the two curve refitting functions generally used to review and verify curve refitting criteria. As the user constructs the initial calibration, they see these calibration metrics change real time with each calibration decision point change. As discussed earlier, the software incorporates calibration evaluation parameters not currently programed into on-boarded instrument software, i.e., RSE, PE %, etc.

WLTR allows the user to input initial calibration criteria for each calibration evaluation parameter including RSE and PE %. These values are calculated and displayed on the data visualization deck (DVD) as well as the initial calibration summary table. WLTR calculates PE % bias results for each calibration point for all mathematical options for each target analyte. Initial calibration points having a calculated bias greater than the value chosen by the user will be flagged. WLTR also evaluates the RSE value for the chosen mathematical model and displays that information on the data visualization deck and in the initial calibration summary table. WLTR deconstructs the PE % results and displays that data in the Linear Dynamic Range (LDR) Study report for each target analyte.

Identifying ICAL Data Issues and Final Documentation. WLTR incorporates these novel architectural software design features which allow the user to quickly compute, construct, display, review, select and evaluate initial calibration model selection. WLTR independently calculates the initial calibration mathematical models for each target analyte using the "raw" data uploaded into the SAAS program.

This program will produce true independent validation of the initial calibration. WLTR summarizes the initial calibration using the method evaluation parameters and the user selected evaluation criteria in the initial calibration evaluation table. This allows the user to identify initial calibration data issues as well as final documentation of the initial calibration.

A Metadata Approach to Construct Best-Fit Initial Calibration Models Achieving Better Decision Outcomes. WLTR as a mathematically based SAAS program will independently compute, construct, and display the initial calibration for each target analyte. This program then uses logic functions to review and select calibration variables against evaluation parameters. WLTR then takes a metadata approach using logic functions to evaluate, validate and document all major and minor construction variables chosen by the user for each target analyte. WLTR is a user friendly tool performing all of the calculations independent of the on-boarded software and displays that information on a data visualization deck (DVD) (i.e. platform, table) that is truly unique. WLTR is the answer to questions centering around software limitations users encounter with on-boarded instrument software.

Driving Profitability. This field needs a solution to review, verify and validate the initial calibration, produced from the instrument on-boarded software, using a program that independently calculates the calibration parameters and evaluates the initial calibration against chosen calibration criteria. WLTR incorporates novel software design features drives financial profit metrics as follows: 1) analysts can make initial calibrations construction decisions exponentially faster, 2) calibration issues or problems will be flagged by the software enabling the analyst to reevaluate those initial decisions producing far fewer mistakes, 3) better fit initial calibrations will produce better data quality, 4) better quality data lowers the laboratories exposure to liability issues, and 5) translates to higher corporate profits.

Cost Savings, Increase in Staff Efficiency and Quality. Without implementing the software application 10, to calibrate a volatile organic compound (VOC) instrument with a 70 compound target analyte list would take approximately 14 to 16 hours with an average bench chemist and no other mitigating issues. The result is a calibration that has been paper reviewed with no mathematical data validation at all.

With the software application 10, approximate times for the process are as follows: loading data (15 minutes); entering method variables for calibration evaluation (10 minutes); initial Cal Res review and selection of calibration models (2 minutes per analyte=70×2 minutes=140 minutes); initial Summary Table review (10 minutes); second review and adjustment of the calibration models (15 minutes); print Summary and RF table and update instrument (20 minutes); requantitate the ICV against the instrument software (5 minutes); load the ICV into the software application 10 and re-valuate (20 minutes). The total estimated time for calibration is four hours or less. A gas chromatography mass spectrometry (GC/MS) semi-volatile organic compound (SVOC) may need to be recalibrated monthly whereas a VOC instrument may need to be recalibrated 3-4 times a year. A SVOC also is much harder to harder to maintain calibration and generally takes approximately 16 to 18 hours. The difference between the VOC and SVOC is that the SVOC are poorer_behaving analytes. Thus, the decision-making process is a little longer.

Saving time in calibration also produces significant cost savings. A lab with 4 GC/MS VOC would run 12 to 16 calibrations annually. On average it takes between 14 to 16 hours to complete this process. Using an average hourly wage of an analyst of $35 per hour, the low range estimated cost savings is $4200 and the high range savings is $6720. A lab with 1 GC/MS SVOC would run approximately 12 calibrations annually. On average it takes 16 to 18 hours to calibrate this instrument. The low range estimated savings is $5040 and the high range savings is $5880. A small lab with 4 GC/MS VOC and 1 SVOC instrument could produce potential annual savings with a low estimate of $9240 and a high estimate of $12,600. Most instruments have a 20-year life cycle so a small laboratory estimated cost savings could approach $200,000. An estimate of 4000 to 5000 laboratories in the US that engage in chromatography is a reasonable guess. Therefore, an estimate of 5000 laboratories engaged in analytical chromatography services would yield a gross savings of 5000*$10,000=$50 million annually. The true cost savings is likely to be 3 to 5 times that value as these estimates are predicated using the metrics of a small laboratory. Most laboratories also have HPLC, GC/FID, GC/PID, GC/ECD IC etc., so the $10,000 annual saving is most likely north of that value.

What is claimed is:
1. A method for providing quality assurance for validation of calibration data comprising:
 a. providing an analytical instrument with analytical instrument software;
 b. uploading, by a user, a first data set acquired by the analytical instrument, wherein the first data set comprises raw data and includes a plurality of target analytes, into a software application installed on a computing device;
 c. uploading, by the user, a second data set acquired by the analytical instrument, wherein the second data set comprises initial calibration verification (ICV) standards and includes the plurality of target analytes, into the software application;
 d. inputting, by the user, a plurality of calibration variables for constructing a calibration curve for each target analyte;
 e. inputting, by the user, evaluation criteria for evaluating the plurality of calibration variables against a plurality of evaluation parameters;
 f. computing mathematically, by the software application, constructed calibration curves for each target analyte, using the plurality of calibration variables and a plurality of mathematical models;
 g. displaying, by the software application, mathematically computed concentration values in a data visualization table, using the first data set uploaded by the user, for each target analyte, for a plurality of selected calibration points, and for a plurality of calibration models;
 h. reviewing, by the user, a plurality of calibration model grades displayed in the data visualization table and summarized in a report card for each target analyte;
 i. selecting, by the user, a mathematical model from the plurality of mathematical models for each target analyte;
 j. evaluating an initial calibration of the analytical instrument, by the software application, using the selected mathematical model for each target analyte and for the plurality of evaluation parameters using the inputted evaluation criteria;
 k. displaying an initial calibration summary table, wherein the initial calibration summary table comprises evaluation metrics which include the plurality of evaluation parameters and the inputted evaluation criteria used during the initial calibration evaluation;

l. displaying an initial calibration evaluation table, wherein the initial calibration evaluation table comprises a list of:
  i. each target analyte; and
  ii. whether each target analyte passed the plurality of evaluation parameters for the inputted evaluation criteria;
m. displaying an initial calibration response factor (RF) summary table, wherein the initial calibration RF summary table comprises a list of:
  i. each target analyte;
  ii. a calculated RF for each target analyte;
  iii. the plurality of evaluation parameters corresponding to each target analyte; and
  iv. the selected mathematical model;
n. updating the analytical instrument software, by the user, wherein updates include: an analytical instrument software method file, and the plurality of calibration variables identified by the software application as meeting the inputted evaluation criteria for the plurality of evaluation parameters for each target analyte;
o. producing, by the analytical instrument software, a calculated concentration value for each target analyte based on the plurality of evaluation variables corresponding to each target analyte;
p. clearing, by the user, the second data set uploaded into the software application and used during the initial calibration evaluation;
q. requantitating, by the analytical instrument software, the second data set for each target analyte using: an updated analytical instrument software method file, and a calculated concentration value for each target analyte based on the plurality of calibration variables identified as meeting the inputted evaluation criteria for the plurality of evaluation parameters corresponding to each target analyte;
r. loading, by the user, the re-quantitated second data set for each target analyte into the software application;
s. producing, by the software application, a calculated ICV concentration value for each target analyte based on the plurality of calibration variables identified as meeting the inputted evaluation criteria for the plurality of evaluation parameters corresponding to each target analyte;
t. comparing, by the software application, calculated ICV concentration values produced by the analytical instrument software and calculated ICV concentration values produced by the software application; and
u. modifying, by the software application, one or more calibration variables, thereby improving the initial calibration of the analytical instrument, to ensure the plurality of evaluation parameters pass the inputted evaluation criteria.

2. The method of claim 1 further comprising: documenting the initial calibration summary table, wherein the initial calibration summary table displays final decisions detailing the initial calibration.

3. The method of claim 1, wherein the analytical instrument software and the software application are configured to perform internal calibrations.

4. The method of claim 1, wherein the analytical instrument software and the software application are configured to perform external calibrations.

5. The method of claim 1, wherein the analytical instrument software and the software application are configured to perform isotope dilution calibrations.

6. The method of claim 1, wherein the initial calibration evaluation table further comprises a list of: ranking a performance of the plurality of evaluation parameters for the inputted evaluation criteria.

7. The method of claim 1, wherein the software application further comprises an extrapolation calculator.

8. A system for providing quality assurance for validation of calibration data comprising:
  a. an analytical instrument comprising analytical instrument software;
  b. a software application installed on a computing device;
  c. a user uploads, into the software application, a first data set acquired by the analytical instrument, wherein the first data set comprises raw data and includes a plurality of target analytes;
  d. the user uploads, into the software application, a second data set acquired by the analytical instrument, wherein the second data set comprises initial calibration verification (ICV) standards and includes the plurality of target analytes;
  e. the user inputs a plurality of calibration variables for constructing a calibration curve for each target analyte;
  f. the user inputs evaluation criteria for evaluating the plurality of calibration variables against a plurality of evaluation parameters;
  g. the software application mathematically computes constructed calibration curves for each target analyte, using the plurality of calibration variables and a plurality of mathematical models;
  h. the software application displays mathematically computed concentration values, using the first data set inputted by the user, for each target analyte, for a plurality of selected calibration points, and for a plurality of calibration models;
  i. the user reviews a plurality of calibration model grades displayed in a data visualization table and summarized in a report card for each target analyte;
  j. the user selects a mathematical model from the plurality of mathematical models for each target analyte;
  k. the software application evaluates an initial calibration of the analytical instrument using the selected mathematical model for each target analyte and for the plurality of evaluation parameters using the inputted evaluation criteria;
  l. the software application displays an initial calibration summary table, wherein the initial calibration summary table comprises evaluation metrics which include the plurality of evaluation parameters and the inputted evaluation criteria used during the initial calibration evaluation;
  m. the software application displays an initial calibration evaluation table, wherein the initial calibration evaluation table comprises a list of:
    i. each target analyte; and
    ii. whether each target analyte passed the plurality of evaluation parameters for the inputted evaluation criteria;
  n. the software application displays an initial calibration response factor (RF) summary table, wherein the initial calibration RF summary table comprises a list of:
    i. each target analyte;
    ii. a calculated RF for each target analyte;
    iii. the plurality of evaluation parameters corresponding to each target analyte; and
    iv. the selected mathematical model;
  o. the user updates the analytical instrument software, wherein updates include: an analytical instrument software method file, and the plurality of calibration variables identified by the software application as meeting the inputted evaluation criteria for the plurality of evaluation parameters for each target analyte;

p. the analytical instrument software produces a calculated concentration value for each target analyte based on the plurality of evaluation variables corresponding to each target analyte;

q. the user clears the second data set uploaded into the software application and used during the initial calibration evaluation;

r. the analytical instrument software re-quantitates the second data set for each target analyte using: an updated analytical instrument software method file, a calculated concentration value for each target analyte based on the plurality of calibration variables identified as meeting the inputted evaluation criteria for the plurality of evaluation parameters corresponding to each target analyte;

s. the user uploads the re-quantitated second data set for each target analyte into the software application;

t. the software application produces a calculated ICV concentration value for each target analyte based on the plurality of calibration variables identified as meeting the inputted evaluation criteria for the plurality of evaluation parameters corresponding to each target analyte;

u. the software application compares calculated ICV concentration values produced by the analytical instrument software and calculated ICV concentration values produced by the software application; and v. the user modifies one or more calibration variables, thereby improving the initial calibration to ensure the plurality of evaluation parameters have passed the inputted evaluation criteria.

9. The system of claim 8 further comprising: the user documents the initial calibration summary table, wherein the initial calibration summary table displays final decisions detailing the initial calibration.

10. The system of claim 8, wherein the analytical instrument software and the software application are configured to perform internal calibrations.

11. The system of claim 8, wherein the analytical instrument software and the software application are configured to perform external calibrations.

12. The system of claim 8, wherein the analytical instrument software and the software application are configured to perform isotope dilution calibrations.

13. The system of claim 8, wherein the initial calibration evaluation table further comprises a list of: ranking a performance of the plurality of evaluation parameters for the inputted evaluation criteria.

14. The system of claim 8, wherein the software application further comprises an extrapolation calculator.

* * * * *